United States Patent
Kallis

(10) Patent No.: US 8,406,892 B2
(45) Date of Patent: Mar. 26, 2013

(54) METHOD AND APPARATUS FOR DETECTING IMMINENT STRUCTURAL FAILURE OF AN ELECTRICAL LEAD IN AN IMPLANTED CARDIAC THERAPY MEDICAL DEVICE

(75) Inventor: James M. Kallis, Los Angeles, CA (US)

(73) Assignee: Kallis Technical Services, Los Angeles ( * ) Notice: Subject to any disclaimer, the term of this patent is extended or adjusted under 35 U.S.C. 154(b) by 621 days.

(21) Appl. No.: 12/653,423

(22) Filed: Dec. 11, 2009

(65) Prior Publication Data

US 2010/0318141 A1 Dec. 16, 2010

Related U.S. Application Data

(60) Provisional application No. 61/268,699, filed on Jun. 15, 2009.

(51) Int. Cl.
*A61N 1/00* (2006.01)
(52) U.S. Cl. ............... 607/60; 607/63; 607/27
(58) Field of Classification Search .......... 607/8, 27–28, 607/122, 116
See application file for complete search history.

(56) References Cited

U.S. PATENT DOCUMENTS

| | | | |
|---|---|---|---|
| 4,899,750 A | 2/1990 | Ekwall | |
| 5,549,646 A | 8/1996 | Katz et al. | |
| 5,741,311 A | 4/1998 | McVenes et al. | |
| 5,755,742 A * | 5/1998 | Schuelke et al. | 607/27 |
| 5,814,088 A * | 9/1998 | Paul et al. | 607/28 |
| 5,837,900 A | 11/1998 | Lipson | |
| 6,317,633 B1 | 11/2001 | Jorgenson et al. | |
| 6,721,600 B2 * | 4/2004 | Jorgenson et al. | 607/27 |
| 7,369,893 B2 | 5/2008 | Gunderson | |
| 2004/0054390 A1 * | 3/2004 | Zarembo et al. | 607/122 |
| 2006/0089691 A1 * | 4/2006 | Kaplan et al. | 607/116 |
| 2006/0089692 A1 * | 4/2006 | Cross et al. | 607/116 |
| 2006/0089695 A1 * | 4/2006 | Bolea et al. | 607/122 |
| 2006/0089696 A1 * | 4/2006 | Olsen et al. | 607/122 |
| 2006/0089697 A1 * | 4/2006 | Cross et al. | 607/122 |

OTHER PUBLICATIONS

Kallinen et al., "Failure of impedance monitoring to prevent adverse clinical events caused by fracture of a recalled high-voltage implantable cardioverter-defibrillator lead", Heart Rhythm, vol. 5, pp. 775-779, 2008, Washington, DC.
Farwell et al., "Accelerating risk of Fidelis lead fracture", Heart Rhythm, published online Jul. 4, 2008, Washington, DC.
Medtronic, Inc., News Release, Sep 4, 2008, Minneapolis, MN.
Kallis, Heart Rhythm, vol. 6, No. 1, pp. e5-e6, Jan. 2009, Washington, DC.
Hauser et al., Heart Rhythm, vol. 6, No. 1, p. e6, Jan 2009, Washington, DC.
Wikipedia, "Implantable Cardioverter-Defibrillator", Apr. 23, 2009, http://en.wikipedia.org/wiki/Implantable_cardioverter-defibrillator.

* cited by examiner

*Primary Examiner* — Eric D. Bertram
*Assistant Examiner* — Roland Dinga
(74) *Attorney, Agent, or Firm* — Lewis B. Sternfels

(57) ABSTRACT

A method and apparatus implementing the method, which is not dependent on monitoring the electrical impedance of the lead, detects imminent structural failure of an electrical lead in an implanted medical device, such as an implantable cardioverter-defibrillator (ICD) or a pacemaker. The approach is to monitor directly the mechanical load loss of the lead (a measure of the loss of structural integrity of the lead) rather than, as in the prior art, to infer it from the electrical impedance.

16 Claims, 3 Drawing Sheets

METHOD AND APPARATUS FOR DETECTING IMMINENT STRUCTURAL FAILURE OF AN ELECTRICAL LEAD IN AN IMPLANTED CARDIAC THERAPY MEDICAL DEVICE

CROSS-REFERENCE TO RELATED APPLICATION

This application claims the benefit of U.S. Provisional Application No. 61/268,699, filed 15 Jun. 2009.

REFERENCE REGARDING FEDERAL SPONSORSHIP

Not Applicable

REFERENCE TO MICROFICHE APPENDIX

Not Applicable

FIELD OF THE INVENTION

The present invention relates to a cardiac therapy medical device implanted in a patient, such as an implantable cardioverter-defibrillator (ICD) or pacemaker and, more particularly, to detecting imminent lead failure in such an implanted medical device by post-implant monitoring.

DESCRIPTION OF RELATED ART AND OTHER CONSIDERATIONS

A key component of an implanted medical device, such as an ICD or pacemaker, is the electrical lead. Such leads typically consist of electrical conductors, which are electrically isolated from each other by insulation. A set of such insulated conductors is encased in an outer sheath of insulation.

Failure of the lead can have adverse, even fatal, clinical consequences for the patient. Failure mechanisms include insulation failure and fracture of a conductor.

The medical device industry uses electrical measurements, such as lead electrical impedance, to determine that failure of an implanted medical device (e.g., ICD or pacemaker) lead is imminent. In the prior art, the impedance is monitored and is compared with the impedance at the time the device was implanted in the patient. If the impedance changes by a specified amount, the lead is considered to be on the verge of failure and corrective action is warranted to prevent a lead failure that could harm the patient.

Prior art methods for detection of lead related conditions based on impedance monitoring are disclosed in the following U.S. Patents:

| | | | |
|---|---|---|---|
| 4,899,750 | February 1990 | Ekwall | 128/419 PG |
| 5,549,646 | August 1996 | Katz et al. | 607/8 |
| 5,741,311 | April 1998 | Mc Venes et al. | 607/28 |
| 5,755,742 | May 1998 | Schuelke et al. | 607/27 |
| 5,814,088 | September 1998 | Paul et al. | 607/28 |
| 5,837,900 | November 1998 | Lipson | 73/661 |
| 6,317,633 | November 2001 | Jorgensen et al. | 607/28 |
| 7,369,893 | May 2008 | Gunderson | 607/27 |

All of these patents are incorporated by reference.

However, clinicians report that electrical impedance monitoring has only limited effectiveness for preventing adverse clinical events, specifically inappropriate shocks, resulting from fracture of ICD leads (Kallinen et al., "Failure of impedance monitoring to prevent adverse clinical events caused by fracture of a recalled high-voltage implantable cardioverter-defibrillator lead", Heart Rhythm, Vol. 5, pp. 775-779, 2008; Farwell et al., "Accelerating risk of Fidelis lead fracture", Heart Rhythm, published online 4 Jul. 2008).

Kallis explained these findings by pointing out that electrical impedance has been found to be an insensitive measure of imminent structural failure of an electrical connection (Kallis, Heart Rhythm, Vol. 6, No. 1, pp. e5-e6, January 2009).

In 2008, device manufacturer Medtronic, Inc., tried to solve the problem by revising the algorithm for detecting lead failure. Medtronic calls this software upgrade, which it claims " . . . gives patients advance notice of a potential lead fracture", Lead Integrity Alert™ (Medtronic News Release, Sep. 4, 2008).

The Minneapolis Heart Institute states that the " . . . new lead monitoring algorithm . . . incorporates both impedance and noise detection. When significant impedance changes or noise is detected, the pulse generator automatically changes its tachycardia detection criterion to 30 of 40 intervals and initiates a series of audible alerts. Based on its bench tests, the manufacturer expects that this new algorithm will provide a 2- to 3-day advance warning before a lead fracture causes an adverse event, such as inappropriate shocks. Although clinical data regarding the safety and efficacy of the algorithm are needed, we are encouraged by our initial experience with this new monitoring technique for detecting Sprint Fidelis pace-sense conductor fractures" (Hauser et al., Heart Rhythm, Vol. 6, No. 1, p. e6, January 2009). However, Hauser et al. also point out a disadvantage of the new lead monitoring algorithm: "Physicians should recognize that prolonging the number of intervals to detect a ventricular tachyarrhythmia will delay therapy, which, for some patients, may be unsafe."

Therefore, a novel approach to how lead failure is detected by post-implant monitoring is warranted. A measure of imminent structural failure of an implanted lead more sensitive than impedance has the potential benefit of earlier detection of lead failure.

SUMMARY OF THE INVENTION

This invention is a method, not dependent on monitoring the electrical impedance of the lead, for detecting imminent structural failure of an electrical lead in an implanted medical device, such as an implantable cardioverter-defibrillator (ICD) or a pacemaker. The approach is to monitor directly the mechanical load loss of the lead (the decrease in the mechanical load required to deflect/elongate the lead by a specified amount, which is a measure of the loss of structural integrity of the lead) rather than, as in the prior art, infer it from the electrical impedance. The invention includes apparatus for implementing the method.

DETAILED DESCRIPTION OF THE INVENTION

The principle is to exploit, that is, to take advantage of the stresses and strains placed on the lead which are produced by ordinary movements of the patient by monitoring and measuring the mechanical load versus the lead deflection as a function of time after implantation. A decrease in the mechanical load resulting from a deflection and/or elongation (that is, an event that results in a mechanical load loss) indicates that the structural integrity of the lead has decreased such as, for example, resulting from a crack occurring or growing in the structure. A decrease that exceeds a specified threshold indicates imminent structural failure and triggers an alarm to the patient.

These stresses and/or strains, which are produced by everyday movements of the patient, occur because of where the cardiac therapy medical device is implanted or placed in the patient. The United States Government websites show the placement of the ICD in the upper left chest of the patient, as shown by indicium 10 in FIG. 1. (The US NHLBI (National Heart, Lung, and Blood Institute, National Institutes of Health), states that an ICD is placed in the chest or abdomen (www.nhlbi.nih.gov/health/dci/Diseases/icd/icd_whatis.html), but shows only placement in the upper left chest.) Thus the upper left chest appears to be the typical location.

Figure 1:
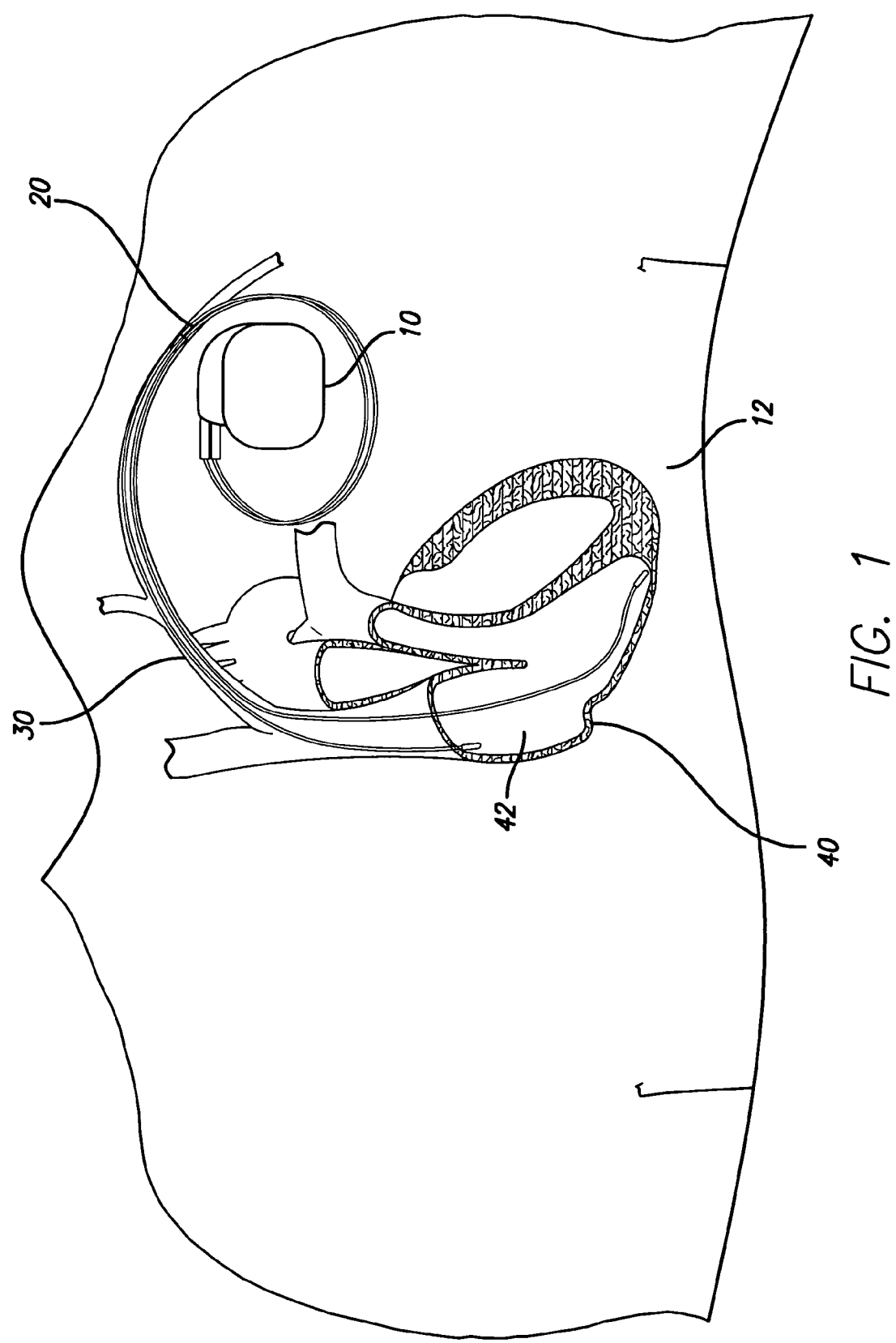
FIG. 1 is a sketch of an ICD implanted into a patient's heart.

As shown in FIG. 1, ICD 10 is implanted in the upper left chest (as shown by indicium 12) of the patient, and a lead 20 is inserted into a vein 30 leading to the patient's heart 40 and from there into its right ventricle (42).

Verification that movements by the patient produced stresses on the lead is provided by the following quotations:
1. "Cardiac lead bodies are continuously flexed by the beating of the heart . . . Movements by the patient can cause the route traversed by the lead body to be constricted or otherwise altered causing stresses on the lead body." (Gunderson, U.S. Pat. No. 7,369,893 B2 (May 6, 2008))
2. "Almost all forms of physical activities can be performed by patients with an ICD. All forms of sports that do not pose a risk of damaging the ICD can be enjoyed by the patient. Special care should be placed not to put excessive strain on the shoulder, arms, and torso area where the ICD is implanted. Doing so may damage the ICD or the leads going from the unit to the patient's heart." ("Implantable Cardioverter-Defibrillator", Wikipedia, 23 Apr. 2009 (http://en.wikipedia.org/wiki/Implantable_cardioverter-defibrillator))

Figure 2:
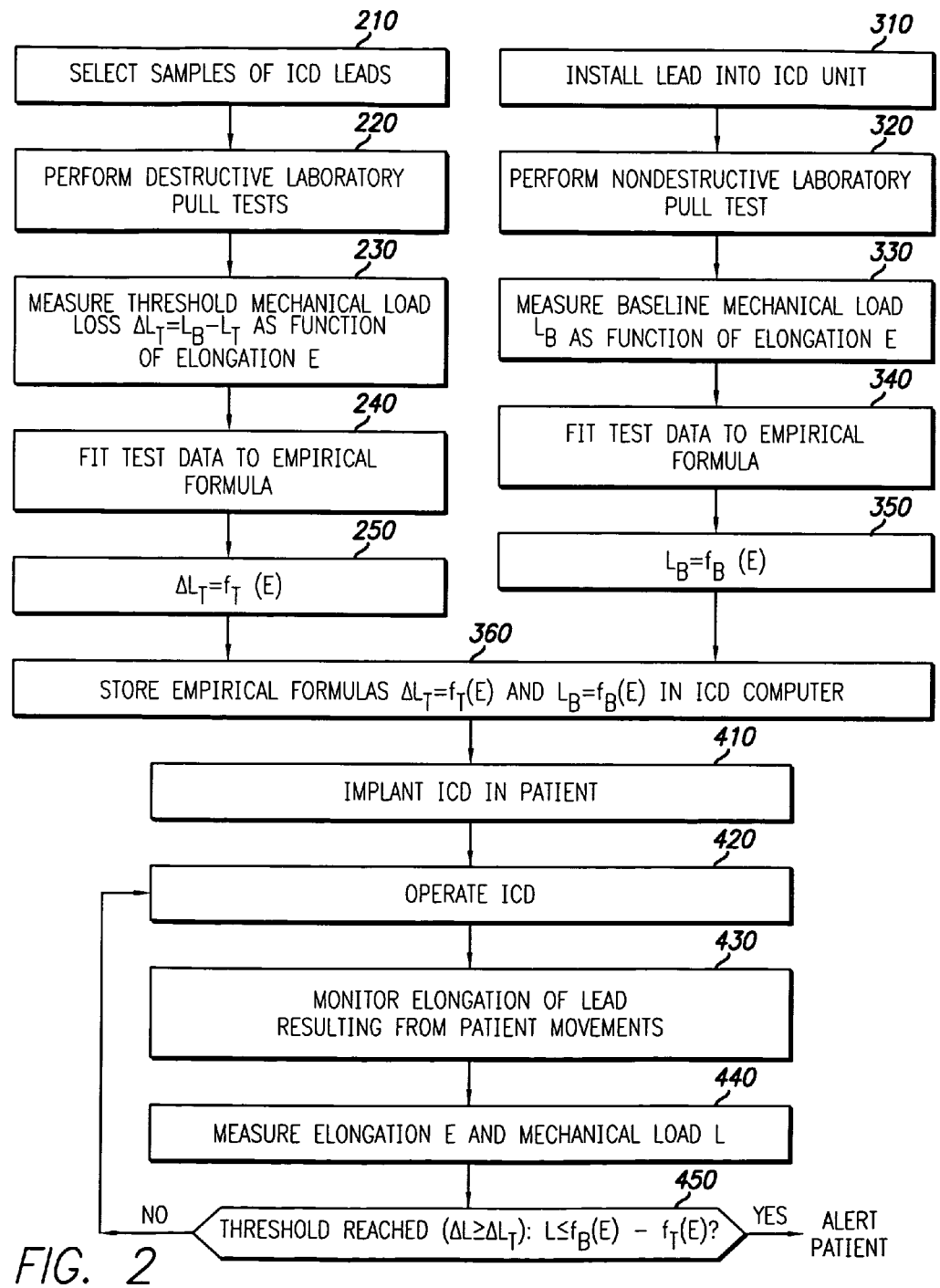
FIG. 2 is a flow chart describing the steps in the method.

The method of the invention is to implement this principle by establishing two deflection or elongation versus mechanical load relationships, as obtained from the performance and measuring steps (enclosures 220 and 230) in FIG. 2. For this purpose, the lead assemblies preferably comprise insulated conductors; the purpose of using insulated conductors is to account for the stiffening effect of the insulation on the structural characteristics of the lead.

The first relationship is the threshold mechanical load loss (the difference between the baseline load and the value after stressing) that indicates imminent structural failure.

The first step (enclosure 210) is to select samples of cardiac therapy medical device leads of the model number of interest from the production line. The leads are subjected to destructive laboratory pull testing (enclosure 220) (as described, for example, in US Military Standard 883C, Notice 5, "Test Methods and Procedures for Microelectronics", Method 2011.6 "Bond Strength (Destructive Bond Pull Test)", 29 May 1987). At the start of the testing, the leads are pulled, and the elongation E and the baseline mechanical load $L_B$ are measured. Then flaws are made to grow in the leads, and the measurements are repeated. By this means, the tests result in evaluating the threshold mechanical load $L_T$ and the threshold mechanical load loss $\Delta L_T = L_B - L_T$ as a function of the elongation E (enclosure 230). The threshold test data are fit to an empirical formula (enclosure 240), of the general form $\Delta L_T = f_T(E)$ (enclosure 250). The best-fit function and the best-fit parameters are determined by well known methods (for example, least squares (Ralston, *A First Course in Numerical Analysis*, McGraw-Hill Book Co., New York, 1965, Chapter 6)). The empirical formula is stored in the cardiac therapy medical device computer (enclosure 360). The steps 210-250 and 360 have to be performed only once for a particular lead model.

The second is performed for each serial number of a lead in an implanted device. A baseline is established immediately after the lead is installed into the cardiac therapy medical device during fabrication of the device (enclosure 310). The lead is subjected to a nondestructive laboratory pull test (enclosure 320) (as described, for example, in Manson and Halford, *Fatigue and Durability of Structural Materials*, ASM International, Materials Park, Ohio, pp. 416-422, 2006), in which the elongation E and the baseline mechanical load $L_B$ are measured (enclosure 330). The baseline test data are fit to a formula (enclosure 340), of the form $L_B = f_B(E)$ (enclosure 350). The best-fit function and the best-fit parameters are determined by well known methods (for example, least squares (Ralston, *A First Course in Numerical Analysis*, McGraw-Hill Book Co., New York, 1965, Chapter 6)). The empirical formula is stored in the serial number of the cardiac therapy medical device computer (enclosure 360).

Then the cardiac therapy medical device is implanted in the patient (enclosure 410) and operated (enclosure 420). The cardiac therapy medical device computer continuously monitors elongation of the lead resulting from patient movements (enclosure 430). When an elongation is sensed, the elongation E and corresponding mechanical load L are measured (enclosure 440). The cardiac therapy medical device computer determines whether the threshold for imminent structural failure has been reached by comparing the mechanical load loss $\Delta L = L_B(E) - L$ with the threshold mechanical load loss $\Delta L_T(E)$ (enclosure 450). If $\Delta L > \Delta L_T(E)$, that is, if $L < f_B(E) - f_T(E)$, then the cardiac therapy medical device alerts the patient that structural failure of the lead is imminent. If $\Delta L < \Delta L_T(E)$, that is, if $L > f_B(E) - f_T(E)$, then the cardiac therapy medical device continues to operate. This is the same algorithm as with the prior art, except that the parameter employed is mechanical load loss rather than electrical impedance.

The cardiac therapy medical device computer (enclosure 360) can be an existing cardiac therapy medical device computer, like that shown in FIG. 2 of the prior art patent by Gunderson, U.S. Pat. No. 7,369,893 B2 (May 6, 2008). With the present invention, the computer processes mechanical (elongation and the mechanical load) data on the lead, rather than electrical impedance data.

Figure 3:
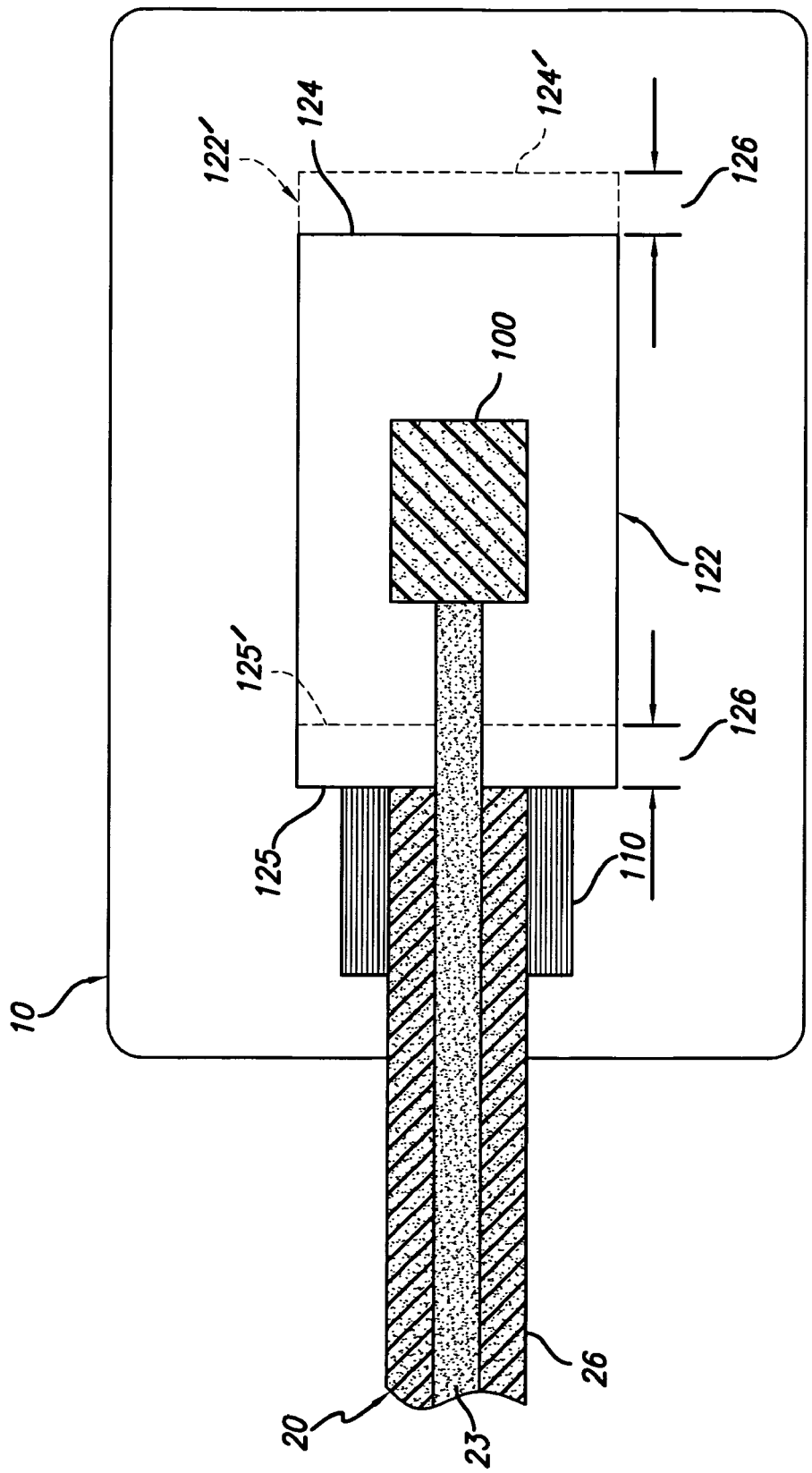
FIG. 3 is a sketch of an embodiment of the apparatus of the invention, incorporated into a cardiac therapy medical device.

In addition to the method, the invention includes apparatus: gauges to measure the elongation and mechanical load of the lead in the implanted device. Cardiac therapy medical devices in the prior art have no such gauges. An exemplary embodiment of the invention is shown in FIG. 3. The gauges are installed at the point where the lead (e.g., lead 20), consisting of a conductor 23 and insulation 26, is connected to the cardiac therapy medical device connector block. The connector block, as indicated by indicium 122, includes, inter alia, end walls 124 and 125. When the connector block is moved, such as by the patient, e.g., in a direction to the right as viewed in the drawing and as denoted by indicium 122' (with walls 124 and 125 moving to their new positions as denoted by dashed lines 124' and 125'), lead 20 is elongated. This elongation is measured by a strain gauge 110, which is bonded to the lead and which is positioned adjacent to and secured to wall 125. As illustrated in FIG. 3, such elongation 126 (which is exaggerated for illustrative purposes) is denoted by the spacing respectively between walls 124 and 124' and walls 125 and 125'. The corresponding mechanical load on the conductor is measured by a force gauge 100. Gauges that can be modified to serve the purposes of gauges 100 and 110, as are described and embodied herein, are commercially available. For example, Endevco Corporation manufactures piezoelectric accelerometers that are implanted in pacemakers to detect patient activity, such as motion. Endevco also manufactures silicon piezoresistive pressure gauges, which are designed to measure fluid pressure; they are modifiable to measure force and deflection/elongation and sealed for use in implanted medical devices. Vishay Micro-Measurements manufactures metal foil piezoresistive strain gauges, suitable for the elongation gauge 110. FUTEK Advanced Sensor Technology, Inc., manufactures force gauges (also called force sensors, force transducers, or load cells), consisting of arrays of Vishay® (registered trademark of Vishay Intertechnology, Inc.) metal foil strain gauges that are electrically connected to form a Wheatstone bridge circuit. The sensors, including the associated electronics, can be miniaturized to the diameter of a shirt button. FUTEK sensors have been implanted in human knees and in bladders for urinary control. The implanted bladder device is a blocking oscillator electrical circuit consisting of (1) a silicon nitride membrane pressure sensor with integrated piezoresistors and (2) an integrated circuit, both mounted on a printed circuit board. The device is coated with silicone to render it biocompatible.

Although the invention has been described with respect to particular embodiments thereof, it should be realized that various changes and modifications may be made therein without departing from the spirit and scope of the invention.

What is claimed is:

1. In a cardiac therapy medical device implanted in a patient wherein the medical device has electrical leads subject to structural failure, a method for detecting imminent structural failure of any of the electrical leads in the implanted medical device comprising the step of directly monitoring mechanical load loss parameters that are indicative of any loss of structural integrity of the electrical leads.

2. The method according to claim 1 in which said monitoring step includes the step of detecting any deflection and/or elongation of the electrical leads resulting from movement of the patient.

3. The method according to claim 2 wherein the medical device comprises an implantable cardioverter-defibrillator.

4. The method according to claim 2 wherein the medical device comprises a pacemaker.

5. In a cardiac therapy medical device implanted in a patient wherein the medical device has electrical leads subject to structural failure, a method for detecting imminent structural failure of any of the electrical leads in the implanted medical device comprising the step of directly monitoring any loss of structural integrity of the electrical leads, in which said monitoring step comprises the step of monitoring directly the mechanical load loss of the lead as detected in any decrease in the mechanical load required to deflect and/or elongate the electrical leads by a specified amount.

6. In a cardiac therapy medical device implanted in a patient wherein the medical device has electrical leads subject to structural failure, a method for detecting imminent structural failure of any of the electrical leads in the implanted medical device comprising the step of directly monitoring any loss of structural integrity of the electrical leads in which said monitoring step comprises the step of detecting the decrease in the mechanical load required to deflect or elongate the electrical leads by a specified amount.

7. In a cardiac therapy medical device implanted in a patient wherein the medical device has electrical leads subject to structural failure, a method for detecting imminent structural failure of any of the electrical leads in the implanted medical device comprising the step of directly monitoring any loss of structural integrity of the electrical leads in which said monitoring step comprises the step of measuring the mechanical load on the electrical leads versus deflection of the lead as a function of time after implantation.

8. A cardiac therapy medical device implanted in a patient wherein the medical device has at least one electrical lead subject to structural failure, a monitor for detecting imminent structural failure of the electrical lead in the implanted medical device comprising measuring apparatus coupled to the electrical lead and the medical device for directly monitoring mechanical load loss parameters that are indicative of any loss of structural integrity of the electrical leads.

9. The device according to claim 8 in which said measuring apparatus includes a mechanism for measuring the mechanical load loss of the electrical lead.

10. The device according to claim 9 in which said mechanism includes implementation for measuring the loss of structural integrity of the electrical lead.

11. The device according to claim 8 in which said measuring apparatus includes a mechanism for detecting any deflection and/or elongation of the electrical lead resulting from movement of the patient.

12. The device according to claim 8 wherein the medical device comprises an implantable cardioverter-defibrillator.

13. The device according to claim 8 wherein the medical device comprises a pacemaker.

14. A cardiac therapy medical device implanted in a patient wherein the medical device has at least one electrical lead subject to structural failure, a monitor for detecting imminent structural failure of the electrical lead in the implanted medical device comprising measuring apparatus coupled to the electrical lead and the medical device for directly monitoring any loss of structural integrity of the electrical leads, in which said measuring apparatus comprises a mechanism for directly measuring the mechanical load loss of the lead as detected in any decrease in the mechanical load required to deflect and/or elongate the electrical lead by a specified amount.

15. A cardiac therapy medical device implanted in a patient wherein the medical device has at least one electrical lead subject to structural failure, a monitor for detecting imminent structural failure of the electrical lead in the implanted medical device comprising measuring apparatus coupled to the electrical lead and the medical device for directly monitoring any loss of structural integrity of the electrical leads, in which said measuring apparatus comprises a mechanism for detecting any decrease in the mechanical load required to deflect or elongate the electrical lead by a specified amount.

16. A cardiac therapy medical device implanted in a patient wherein the medical device has at least one electrical lead subject to structural failure, a monitor for detecting imminent structural failure of the electrical lead in the implanted medical device comprising measuring apparatus coupled to the electrical lead and the medical device for directly monitoring any loss of structural integrity of the electrical leads, in which said mechanism includes implementation for measuring the mechanical load on the electrical lead versus deflection of the lead as a function of time after implantation.

* * * * *